(12) United States Patent
Kimball et al.

(10) Patent No.: US 7,378,408 B2
(45) Date of Patent: May 27, 2008

(54) METHODS OF TREATMENT AND FORMULATIONS OF CEPHALOSPORIN

(75) Inventors: Roger N. Kimball, Waterford, CT (US); Renuka D. Reddy, Waterford, CT (US); Evgenyi Y. Shalaev, Old Lyme, CT (US)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 423 days.

(21) Appl. No.: 10/292,343

(22) Filed: Nov. 12, 2002

(65) Prior Publication Data

US 2003/0186957 A1 Oct. 2, 2003

Related U.S. Application Data

(60) Provisional application No. 60/398,932, filed on Jul. 26, 2002, provisional application No. 60/338,536, filed on Nov. 30, 2001.

(51) Int. Cl.
*A61K 31/545* (2006.01)
(52) U.S. Cl. ....................... 514/202; 514/970
(58) Field of Classification Search ............... 514/206
See application file for complete search history.

(56) References Cited

U.S. PATENT DOCUMENTS

| | | | |
|---|---|---|---|
| 4,002,748 A | 1/1977 | Bornstein et al. | 424/246 |
| 4,418,058 A | 11/1983 | Hirai et al. | 424/176 |
| 5,138,066 A | 8/1992 | Gotschi | 548/194 |
| 5,401,842 A | 3/1995 | Nassar et al. | 540/222 |
| 6,001,997 A | 12/1999 | Bateson et al. | 540/222 |
| 6,020,329 A | 2/2000 | Bateson et al. | 514/202 |
| 6,077,952 A | 6/2000 | Bateson et al. | 540/300 |

FOREIGN PATENT DOCUMENTS

| | | |
|---|---|---|
| EP | 0134568 | 11/1988 |
| EP | 0327364 | 2/1989 |
| EP | 1178049 | 2/2002 |
| WO | WO 9201696 | 2/1992 |
| WO | WO01/39836 A1 | 6/2001 |

OTHER PUBLICATIONS

K.A. Connors et al., Chemical Stability of Pharmaceuticals, John Wiley & Sons, New York, 1986, p. 305.*
PCS 10965.
Almarsson, et al. "Solid-State Chemistry ofa Novel Carbapenem with a Releasable Sidechaing", *Tetrahedron* 56, 6877-6885 (2000).
Shamblin, et al. "The Chemical Stability of Amorphous Cefoxitin Sodium in the Presence of Glassy Stabilizers", *AAPS Pharm. Sci.* 1(4) (1999).
Mathlouthi, et al. "Rheological Properties of Sucrose", *Sucrose Properties and Applications*. 137 (1995).
Yoshioka, et al. "Temperature Dependence of Biomolecular Reactions Associated with Molecular Mobility in Lyophilized Formulations", *Pharmaceutical Research* 17(8), 925-929 (2000).
Pikal, et al. "Stability Testing of Pharmaceuticals by High-Sensitivity Isothermal Calorimetry at 25 C: Cephalosporins in the Solid and Aqueous Solution States", *International Journal of Pharmaceutics* 50, 233-252, (1989).
Bateson, et al. "Nove C-3 Cyclic Ether Cephalosporins and Their Orally Absorbed Prodrug Esters", *The Journal of Antibiotics* 47 (2), 253-256, (1994).
K.P. Flora, J.C. Cradock, G.K. Poochikian, "The loss of paraben preservatives during freeze drying", J. Pharm. Pharmacol. 1980, 32:577.
Connors, et al. Chemical Stability of Pharmaceuticals. New York, NY. John Wiley & Sons, 1986.

* cited by examiner

*Primary Examiner*—Frederick Krass
(74) *Attorney, Agent, or Firm*—Gregg C. Benson; Charles W. Ashbrook; John H. Engelmann

(57) ABSTRACT

Formulations containing an antibacterial alkali metal salt of a cephalosporin compound and methods of treating bacterial infections in dogs and cats.

6 Claims, No Drawings

METHODS OF TREATMENT AND FORMULATIONS OF CEPHALOSPORIN

CROSS-REFERENCE TO RELATED APPLICATION

This application claims priority from provisional applications 60/338,536 filed Nov. 30, 2001 and 60/398,932 filed Jul. 26, 2002.

FIELD OF INVENTION

This invention relates to stable lyophilized formulations containing an antibacterial alkali metal salt of a cephalosporin compound, Compound I, wherein $M^+$ is a cation, $Na^+$, $K^+$ or $Li^+$ (hereinafter "Compound I"). In particular, the invention relates to stable lyophilized formulations of Compound I, wherein $M^+$ is $Na^+$, (6R,7R)-7-[[(2Z)-(2-amino-4-thiazolyl)(methoxyimino) acetyl]amino]-8-oxo-3-[(2S)-tetrahydro-2-furanyl]-5-thia-1-azabicyclo[4.2.0]oct-2-ene-2-carboxylic acid, monosodium salt. The invention also relates to aqueous formulations of Compound I.

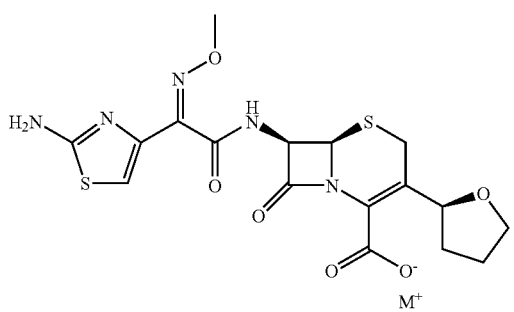

I

The invention is also directed to methods for treating bacterial infections in dogs and cats by administering a compound of Formula I.

BACKGROUND OF THE INVENTION

Cephalosporins are widely used and therapeutically important antibiotics. The compounds of Formula I are broad spectrum cephalosporin antibacterials and are, therefore, useful in the treatment of bacterial infections in animals. (U.S. Pat. No. 6,020,329, Col. 1, lines 13-14). In particular, Compound I is targeted for dogs and cats with indications for treatment of bacterial infections of the skin, soft tissue, periodontal and urinary tract.

Compound I, wherein M is $Na^+$, and the preparation thereof, are disclosed in U.S. Pat. Nos. 6,001,997, 6,020,329 and 6,077,952. The text of the aforementioned patents and all other references cited in this specification are hereby incorporated by reference in their entirety.

Cephalosporin formulations are generally, however, unstable and a variety of different methods exist to increase stability including, inter alia, the adjustment of pH, crystallization, lyophilization, and the addition of stabilizers, such as sugars.

Cephalosporins may be somewhat stabilized within a certain pH range. The optimum pH range varies widely and is unpredictable for different classes of cephalosporins, requiring experimentation and stability tests. For example, Nassar et al., U.S. Pat. No. 5,401,842, disclosed formulations of crystalline cefepime salt buffered with trisodium orthophosphate, sodium bicarbonate, sodium citrate, N-methyl-glucamine and L(+) arginine to a pH of 3.5 to 7.0.

K. A. Conners et al. disclose that cephalothin has a broad stability range from a pH of between 2 to 8. Cepharadine, however, stabilizes at a more acidic pH between 1 to 5. Stability for Cefotaxime is achieved in the pH range of 3 to 7. (K. A. Connors, et al. Chemical Stability of Pharmaceuticals, John Wiley & Sons, New York, 1986, p305).

In some cases, cephalosporin formulations were stabilized by crystallization and lyophilization. For example, Gotschi, U.S. Pat. No. 5,138,066, describes formulations for parenteral administration as lyophilizates or dry powders for dilution with pharmaceutical carriers such as water or isotonic saline.

Bornstein et al, U.S. Pat. No. 4,002,748, disclose methods of preparing essentially amorphous cefazolin by utilizing certain lyophilization techniques, while Daugherty, EP 0327364, describes a lyophilization method to prepare formulations of a crystalline solvate of a 1-carbacephalosporin.

Some cephalosporins may be stabilized by addition of a variety of different sugars. Whether a certain sugar will stabilize a particular cephalosporin, however, is unpredictable. Furthermore, the ratio of sugar to cephalosporin to achieve optimum stability is also unpredictable. For example, Shamblin et al. disclose that the stability of amorphous cefoxitin sodium was improved by a factor of two when co-lyophilized with sucrose. The stability of cefoxitin was not affected, however, when co-lyophilized with trehalose. S. L. Shamblin, B. C. Hancock, M. J.Pikal, The Chemical Stability of Amorphous Cefoxitin Sodium in the Presence of Glassy Stabilizers, AAPS Pharm. Sci. Vol. I, Issue 4, 1999.

Similarly, Shima et al., EP 0134568B1, disclose that sugar (glucose, fructose or maltose) or an alkali metal salt of a mineral acid or carboxylic acid stabilized a specific lyophilized cephalosporin at a 0.01:1 to 0.5:1 weight ratio of stabilizer:cephalosporin. Mannitol, however, was not effective in stabilizing the disclosed cephalosporin compound.

Likewise, Almarsson et al., Tetrahedron 56 (2000) 6877-6885, disclose that sucrose improved chemical stability of a beta-lactam compound at a sucrose/drug ratio of 0.1:1 to 0.5:1.

Yoshioka, Y. et al., Pharm, Res. 17 (2000), 925-929, disclose the stability of cephalothin in the presence of dextran at a dextran/cephalothin ratio of 200:1.

Conversely, Hirai et al., U.S. Pat. No. 4,418,058, disclose that an excess amount, greater than 1:1, of a variety of different sugars or sugar alcohols adversely affected chemical stability of cephalosporins. Good stabilizing results were obtained, however, when the amount of added sugar or sugar alcohol was 0.1 to 1 sugar/cephalosporin.

Consequently, one of ordinary skill in the art cannot, in general, predict whether the addition of a particular sugar to any particular cephalosporin will achieve stability. Moreover, the optimum ratio of sugar:cephalosporin is also highly variable and unpredictable, absent experimentation. Furthermore, as discussed above, the optimum pH range of stability for a particular cephalosporin is also unpredictable.

A method of administration for Compound I is by parenteral administration. Other modes of administration include oral and topical. (U.S. Pat. No. 6,020,329, Col. 15, lines 1-2) Compound I is unstable, as both a solid and an aqueous solution. Furthermore, Compound I is hygroscopic. Consequently, a formulation and method for stabilizing Compound I would be a useful addition to the art.

SUMMARY OF THE INVENTION

In a first aspect, the invention provides a pharmaceutical composition comprising a compound of Formula I,

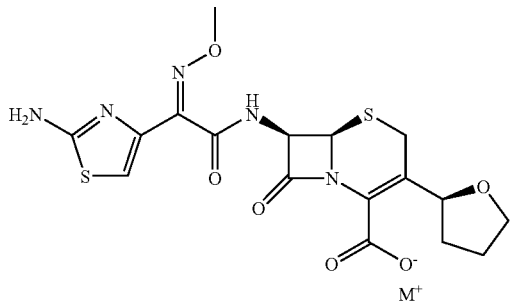

I wherein $M^+$ is $Na^+$, $K^+$ or $Li^+$, and an aqueous diluent, wherein the composition has a pH in the range of 5.0 to 8.0.

In a preferred embodiment, the compound of Formula I is amorphous (6R,7R)-7-[[(2Z)-(2-amino-4-thiazolyl)(methoxyimino) acetyl]amino]-8-oxo-3-[(2S)-tetrahydro-2-furanyl]-5-thia-1-azabicyclo[4.2.0]oct-2-ene-2-carboxylic acid, monosodium salt.

In a preferred embodiment, $M^+$ is $Na^+$ and the pH is 6.0 to 7.5.

In a preferred embodiment, the pharmaceutical composition further comprises a pharmaceutically acceptable buffer.

In a more preferred embodiment, the buffer is carbonate, phosphate, citrate or acetate, and the pH within a range of 6.0 to 7.5.

In a preferred embodiment, the pharmaceutical composition further comprises a pharmaceutically acceptable bulking agent.

In a more preferred embodiment, the bulking agent is selected from sugars, polyalcohols, amino acids, polymers, polysaccharides or inorganic salts.

In a preferred embodiment, the sugars are selected from glucose, maltose, sucrose and lactose; the polyalcohols are sorbitol or mannitol; the amino acid is glycine; the polymer is polyvinylpyrrolidone; the polysaccharide is dextran; and the inorganic salts are sodium or potassium phosphates or sodium chloride.

In a preferred embodiment, the composition has a bulking agent/compound of Formula I ratio greater than 1.0, but less than 100.

In a more preferred embodiment, the ratio is greater than 1, but less than 10.

In a more preferred embodiment, the bulking agent is sucrose and the composition has a sucrose/compound of Formula I ratio of 3.

In another aspect, the invention is directed to a pharmaceutical composition comprising a compound of Formula I,

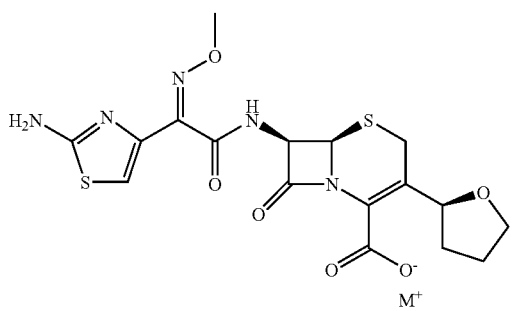

I wherein $M^+$ is $Na^+$, $K^+$ or $Li^+$, an aqueous diluent and a pharmaceutically acceptable bulking agent.

In a preferred embodiment, the bulking agent is selected from sugars, polyalcohols, amino acids, polymers, polysaccharides or inorganic salts.

In a more preferred embodiment, the sugar is selected from glucose, maltose, sucrose or lactose; the polyalcohols are sorbitol or mannitol; the amino acid is glycine; the polymer is polyvinylpyrrolidone; the polysaccharide is dextran; and the inorganic salts are sodium or potassium phosphates or sodium chloride.

In another embodiment, the composition has a bulking agent/compound of Formula I ratio of greater than 1, but less than 10.

In a preferred embodiment, $M^+$ is $Na^+$ and the bulking agent is sucrose, wherein the composition has a sucrose/compound of Formula I ratio of 3.

In a preferred embodiment, the pharmaceutical composition further comprises a pharmaceutically acceptable buffer.

In a preferred embodiment, the pharmaceutical composition further comprises a pharmaceutically acceptable preservative.

In a more preferred embodiment, the preservative is methylparaben, propylparaben, m-cresol, benzalkonium chloride, benzethonium chloride or benzyl alcohol, or a combination of two or more thereof.

In a more preferred embodiment, the preservative is a combination of either (a) methylparaben, propylparaben and benzyl alcohol; or (b) methylparaben and m-cresol.

In another embodiment, the pharmaceutical composition further comprises a citrate buffer.

In another aspect, the invention is directed to a pharmaceutical composition comprising a compound of Formula I,

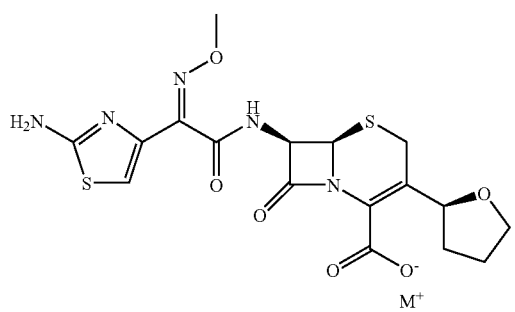

I wherein $M^+$ is $Na^+$, further comprising an optional pharmaceutically acceptable buffer, an optional pharmaceutically acceptable preservative, an optional pharmaceutically acceptable bulking agent and an aqueous diluent, wherein the composition has a pH of 6.0 to 7.5.

In a preferred embodiment, the buffer is citrate; the preservative is methylparaben, propylparaben, m-cresol, benzalkonium chloride, benzethonium chloride or benzyl alcohol or a combination of two or more thereof; and the optional bulking agent is sucrose.

In a preferred embodiment, the pharmaceutical composition comprises a compound of Formula I, prepared by lyophilizing the pharmaceutical composition as described above.

In another aspect, the invention is directed to a kit comprising a) A therapeutically effect amount of a lyophilized pharmaceutical composition comprising a compound I of Formula I;

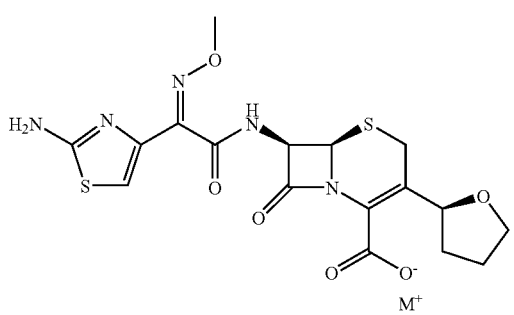

b) An aqueous pharmaceutically acceptable diluent; and
c) A first and second container means for containing the composition (1) and the diluent (2), wherein the first container is adapted to receive the diluent from the second container.

In another aspect, the invention is directed to a method of treating a condition caused by a bacterial infection in dogs and cats, comprising administering a therapeutically effective amount of a compound of Formula I

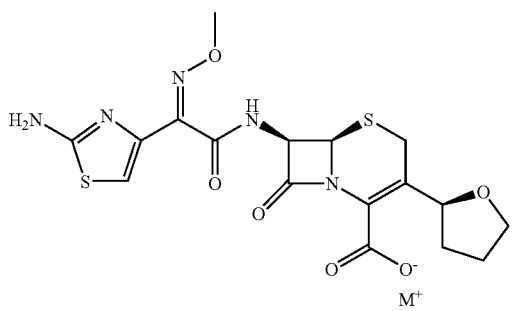

effective in treating such a condition.

In another aspect, the invention is directed to a method of treating a condition caused by a bacterial infection in dogs and cats, comprising administering a therapeutically effective amount of the composition described above.

In one embodiment, the condition is a skin, soft tissue or urinary tract bacterial infection.

In another embodiment, the condition or infection is caused by or complicated by Gram positive or Gram negative bacteria.

The term "about," as used herein, is defined as a pH of 0.5 above or below the designated upper and lower pH units.

The term "aqueous pharmaceutically acceptable diluent" means water or other pharmaceutically acceptable aqueous solutions containing one or more pharmaceutically acceptable excipients for use in making the compositions of the invention (e.g. isotonic solution of sodium chloride, water for injection with ethanol or phosphate, acetate or citrate buffer, and water for injection with benzyl alcohol).

The term "$Na^+$," as used herein, is defined as a sodium cation.

The term "$K^+$," as used herein, is defined as a potassium cation.

The term "$Li^+$," as used herein, is defined as a lithium cation.

The term "composition", as used herein, encompasses, inter alia, (1) solutions comprising Compound I or (2) dry lyophilized residues of such solutions. The solutions may contain one or more optional agents which aid in stabilizing dissolved Compound I and/or that facilitate re-dissolution, upon reconstitution of the lyophile created after lyophilizing solution (1). Such optional agents include, inter alia, bulking agents, preservatives, and buffers, as further disclosed herein.

The term "Compound I" is limited to the pharmaceutically acceptable alkali metal salts of Compound I, wherein $M^+$ is $Na^+$, $K^+$ or $Li^+$, and in particular, includes Compound I, (6R,7R)-7-[[(2Z)-(2-amino-4-thiazolyl)(methoxyimino)acetyl]amino]-8-oxo-3-[(2S)-tetrahydro-2-furanyl]-5-thia-1-azabicyclo[4.2.0]oct-2-ene-2-carboxylic acid, monosodium salt), wherein $M^+$ is $Na^+$.

The term "lyophilization" means the process of freeze-drying a composition as known in the art. "Lyophilized" and "freeze-dried" are used herein as synonyms.

The terms "pharmaceutical" and "pharmaceutically" and the like are meant to refer to applications in both human and veterinary fields.

The term "paraben" as used herein includes those parabens described herein, as well as the salts of those parabens (e.g. sodium salt of propyl paraben).

DETAILED DESCRIPTION OF THE INVENTION

Compound I is a broad spectrum cephalosporin antibacterial targeted for mammals, in particular, dogs and cats. The preparation of Compound I wherein $M^+$ is $Na^+$ (hereinafter the "sodium salt") is described in U.S. Pat. Nos. 6,001,997, 6,020,329, 6,077,952, as well as EP1178049A1; incorporated herein by reference in their entirety. The $K^+$ and $Li^+$ salts of Compound I may be prepared by one of ordinary skill in the art, as described in the preparation of the sodium salt of compound I, but substituting an appropriate $K^+$ or $Li^+$ salt.

The antibiotic compounds of the present invention are active against a wide range of organisms, including both Gram-negative organisms (e.g. *E.coli*), and Gram-positive organisms, (e.g. *S. aureus*). (U.S. Pat. No. 6,020,329, Col 17, lines 28-31). Compound I can be used to treat, inter alia, bacterial infections of the skin, soft tissue and urinary tract. For example, conditions or infections caused by or complicated by Gram positive and/or Gram negative bacteria are: canine pneumonia, feline pneumonia, canine pyoderma, feline pyoderma, pasteurellosis, pneumonia, otitis media, sinusitus, bronchitis, tonsillitis, and mastoiditis associated with infection by *Staphylococcus* spp. (*Staphylococcus intermedius, Staphyloccus aureus*), *Escherichia coli, Streptococcus* spp. (Beta Hemolytic *Streptococcus* spp.), *Pasteurella multocida, Bacteriodes* spp., *Fusobacterium* spp., *Porphyromonas* spp., *Prevotella* spp., *Peptostreptococcus* spp., and *Clostridium* spp., uncomplicated skin and soft tissue infections, abscesses, osteomyelitis, and puerperal fever associated with infection by *Staphylococcus aureus, S. intermedius*, coagulase-positive *staphylococci, S. epidermidis, S. hemolyticus, Streptococcus* ssp, *Streptococcal* groups C-F (minute-colony streptococci), *viridans streptococci*, uncomplicated acute urinary tract infections associated with infection by *Staphylococcus* ssp or *E. coli*; odontogenic infection associated with infection by *viridans streptococci*; urinary tract infection in dogs and cats associated with infection by *E. coli*; skin and soft tissue infections in dogs and cats associated with infection by *Staph. epidermidis, Staph. intermedius*, coagulase neg. *Staph.* or *P. multocida*; infections of the oral cavity in dogs and cats associated with infection by *Alcaligenes* spp., *Bacteroides* spp., *Clostridium* spp., *Enterobacter* spp., *Eubacterium, Peptostreptococcus, Porphyromonas,* or *Prevotella*.

It was determined that the compounds of Formula I, as well as similar compounds disclosed in U.S. Pat. Nos. 6,001,997, 6,020,329 and 6,077,952, exhibit an unexpectedly long half-life in dogs and cats, especially in view of comparable antibiotics. For example, Table I lists well-known antibiotics and their respective half-lives in different mammals, such as in mice, rats, dogs and cats.

TABLE I

Half-life of Known Antibiotics

| Compound | Mouse t½ (h) | Rat t½ (h) | Canine t½ (h) |
|---|---|---|---|
| Cefpodoxime | 0.68 (PO) | 1.4 (PO) | 2.4 (PO) |
| Ampicillin | | 0.84 (IM) | 0.64 (IM) |
| Cefamandole | | 0.5 (IM) | 0.82 (IV) |
| Cefazolin | | 0.66 (IM) | 1.11 (IV) |
| Cefuroxime | 0.32 (SC) | 0.4 (IM) | 0.93 (IM) |
| Cephalordine | | 0.5 (IM) | 0.97 (IM) |
| Cephalothin | 0.208 (IM) | 0.4 (IM) | 1.06 (IM) |
| Cephadrine | | 0.82 (PO) | 3.64 (PO) |
| Erythromycin | 0.65 (IV) | 1.27 (IV) | 1.72 (IV) |
| Oleandomycin | 0.7 (IV) | 0.93 (IV) | 1.53 (IV) |
| Tylosin | | 0.4 (IV) | 1.24 (IV) |

(Cefpodoxime data from "Abstracts of the 1996 ICAAC"; Abstract 593. All other data compiled from: "CRC Handbook of Comparative Pharmacokinetics and Residues of Veterinary Antimicrobials", J. Edmond Riviere; Arthur L. Craigmill, Stephen F. Sundlof CRC Press 1991; Routes of administration: "IV"—intravenous; "IM" = intramuscular; "PO" = per os; "SC" = subcutaneous)

A number of cephalosporin derivatives, including compounds of Formula I, were disclosed in International Patent Application publication number WO 92/01696 and by Bateson et al in The Journal of Antibiotics, February 1994, vol.47, no.2, at pages 253-256. Various mouse data are also disclosed in the latter paper. Both of these publications are herein incorporated in their entirety.

In particular, following administration of the compound of Formula II, the half-life in the mouse and rat were determined to be 2.2 and 3.9 hours, after per os administration, respectively. Unexpectedly, however, in dogs and cats the half-life was in both cases dramatically increased, as is demonstrated below in Table II.

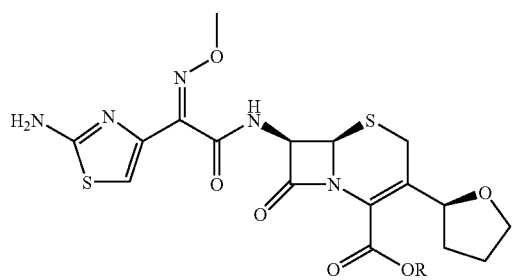

II

TABLE 2

Half-life in Dogs and Cats

| Experiment | Species | Route | Dose[1] (mg/kg) | Compound | Half-life |
|---|---|---|---|---|---|
| 1 | Dog | IV | 1 | Compound of Formula I, M+ = Na | 6.9 days |
| 2 | Dog | SC | 8 | Compound of Formula I, M+ = Na | 4.7 days |
| 3 | Dog | PO | 1 | Compound II, R = pivaloyloxymethyl | 6.0 days |
| 4 | Cat | SC | 8 | Compound of Formula I, M+ = Na | 6.3 days |

Note
[1] Dose expressed as corresponding free acid: i.e. M+ = H. Concentrations measured w.r.t. free acid.

EXPERIMENTAL DETAILS a. Pharmacokinetics

Experiment 1

Intravenous Dog

A male dog was dosed intravenously with an aqueous solution of Compound I. Blood plasma was sampled at times up to 28 days post dosing. Plasma samples were extracted and assayed to determine the concentration by both bioassay and HPLC as follows:

1 mL of plasma (or standards of spiked dog plasma) were acidified to a pH of less than 3 with hydrochloric acid, then shaken with 26 mL of ethyl acetate. The layers were separated by centrifugation. 22 mL of the organic layer was transferred into a fresh container and 2.0 mL of 0.1 M phosphate buffer, pH 7.0, was added. After shaking and centrifugation, the aqueous phase was recovered and assayed. Following processing, samples (and standards) were assayed by hole-in-the-plate microbiological bioassay on large plates (200 mL Mueller Hinton agar) seeded with *M. luteus*. Samples were also assayed by HPLC (μBondapk—C18 column eluted with acetonitrile—0.05M sodium acetate pH 5.0, 15:85, with UV detection at 256 nm). Good agreement was obtained between the two assay methods, and the half-life was calculated from bioassay results using standard pharmacokinetic methods.

Experiment 2

Subcutaneous Dog

Two dogs were dosed with compound of Formula I by subcutaneous injection. Blood plasma was sampled at times up to 28 days post-dosing. Plasma samples and appropriate standards were prepared by deproteination by the addition of an equal volume of acetonitrile and centrifugation (3000 r.p.m. for 10 min.). Supernatant was assayed by a specific HPLC method to determine the concentration (μBondapk—C18 column eluted with acetonitrile—0.05M sodium acetate pH 5.0, 15:85, at 1.0 mL/min with UV detection at 256 nm). Pharmacokinetic parameters were calculated using the program PCNONLIN.

Experiment 3 per os Dog

Six dogs were dosed orally with the pivaloyloxymethyl-ester pro-drug, compound of Formula II, and the resulting plasma concentrations were determined by both bioassay and HPLC. Following dosing, blood plasma was sampled up to 696 hours (29 days). Plasma samples and appropriate standards (1 mL) were first acidified to a pH less than 3.0 with hydrochloric acid then shaken with 30 mL ethyl acetate. The layers were separated by centrifugation then 25 mL of the organic layer was removed. 2 mL of 0.1M phosphate buffer pH 7.0 was added to the ethyl acetate and shaken to effect a back extraction. After separation of the layers, the aqueous phase was removed and used for the assays. Following processing, samples (and standards) were assayed by hole-in-the-plate microbiological bioassay on large plates (200 mL Mueller Hinton agar) seeded with *M. luteus*. Samples were also assayed by HPLC (µBondapk—C18 column eluted with acetonitrile—0.05M sodium acetate pH 5.0, 15:85, at 1.5 mL/min with UV detection at 256 nm). There was good agreement between the two assay methods (r=0.9716) half-life was calculated from the bioassay data.

Experiment 4

Subcutaneous Cat

Four cats were dosed at 8 mg/kg by subcutaneous injection of Compound I. Blood samples were taken at intervals to 35 days post-dosing and the plasma assayed to determine the concentration of the corresponding free acid by HPLC/MS/MS. Plasma samples (100 mL) were aliquotted into centrifuge tubes, then 400 mL of acetonitrile was added. Following vortexing (60 sec.) and centrifugation (20,800× g for 10 minutes), 0.450 mL of the supernatant was transferred into clean centrifuge tubes, and evaporated to dryness at approximately 50° C. under $N_2$. Dried samples were reconstituted in 0.100 mL of mobile phase (15/85 v/v acetonitrile/10 mM $HCO_2NH_4$, pH 3.0), vortexed for 1 minute, centrifuged at 3,000 rpm for 2 minutes, and transferred to an autosampler vial. Single replicates of plasma were analyzed by LC-MS/MS for concentration of compound. Sample analysis was performed on a SCIEX API 365 or 3000 HPLC/MS/MS system. The column effluent was connected to a Turbo-ionspray source set at 4500 V. The collision gas was set to a value of 3. Positive ions were generated in the source and sampled through an orifice into the quadrupole mass filter. The mass spectrometer was adjusted to monitor the precursor and product ions as follows: m/z 454.0–>m/z 241.0. Half-life was calculated using pharmacokinetic program WINNONLIN v2.1 and determined to be 8.39±0.97 days.

b. Efficacy

In an experimentally induced skin infection model study, five out of six dogs had complete clearance of *Staphylococcus intermedius* 15 days after a single administration of 8 mg/kg of the Compound I.

In a separate study, following a single administration of 8 mg/kg Compound I to healthy dogs, there was a significant reduction of the populations of pathogenic *Staphylococci* for four weeks compared to non-treated control animals.

In an experimentally induced abscess model study in cats, there was a substantial reduction in the numbers of *Pasteurella multocida, Clostridium perfringens*, and *Bacteriodes fragilis* bacteria 14 days after a single administration of 8 mg/kg Compound I The above half-life results, together with the potency of the compounds of Formula I, demonstrates that one administration of an equivalent of ca. 4-12 mg/kg of Compound I, (e.g.Na salt of compound of Formula I), given by injection (e.g. intramuscularly, subcutaneously or intravenously), to a cat or dog would advantageously provide an efficacious concentration for 7-21 days. This represents a novel and very convenient treatment regime for veterinary practitioners and cat and dog owners alike.

It has been determined, however, that Compound I is unstable both as a solid and a liquid. In evaluating possible formulations, stability experiments were conducted. As used herein, "stable" or "stabilized" means less than or equal to about 10% decomposition of Compound I.

While many cephalosporins may be stabilized by crystallization, it has been determined that Compound I is not particularly amenable to crystallization techniques on a commercial scale. Consequently, Compound I is in an amorphous state and is hygroscopic. It was determined that optimal long-term stability of Compound I is achieved at a low residual water content. Accordingly, lyophilization of formulations of Compound I provide preferred stability.

With respect to the present invention, stable formulations of Compound I were developed, overcoming the inherent stability problems previously hampering long-term storage goals. It was determined that Compound I could be stabilized and formulated into injectable preparations by formulating Compound I with an aqueous pharmaceutically acceptable diluent, such that the pH is in the range of about 5.0 to about 8.0.

For example, formulations are prepared by dissolving a therapeutically effective amount of the sodium salt of Compound I in an aqueous pharmaceutically acceptable diluent and adjusting the pH, if necessary, to within the range of about 5.0 to about 8.0. Alternatively, the free acid form of Compound I (ie. the carboxylate, instead of the salt) may be utilized as starting material. A suspension or solution of the free acid may be titrated with, for example, sodium hydroxide, forming the sodium salt of Compound I. Adjustments to pH may be conducted as described above.

Aliquots of the resulting solution, the quantity of which is dependent upon the ultimate desired reconstituted concentration of Compound I, are clarified and sterile filtered and aseptically transferred to containers appropriate for lyophilization, (e.g. vials), and partially stoppered with lyo-stoppers. As described hereinafter, the formulation is cooled to freezing, subjected to lyophilization in a manner conventional per se in the art and hermetically capped, forming a stable, dry lyophile formulation. In a preferred embodiment, the composition has a low residual water content, less than 1% by weight, based on the weight of the lyophile. In a more preferred embodiment, the composition has a residual water content level of less than 0.5% by weight.

As used herein, a "therapeutically effective amount" for a dosage unit may typically about 50 to about 500 mg of active ingredient. (U.S. Pat. No. 6020,329; Col 16, line 3). The dose may vary, however, depending on the species, variety, etc. of animal to be treated, the severity and type of infection and the body weight of the animal. Accordingly, based upon body weight, typical dose ranges of the active ingredient may be from about 0.01 to about 100 mg per kg of body weight of the animal. Preferably, the range is from about 1 to about 20 mg per kg of body weight, and more preferably, from about 4 to about 12 mg per kg of body weight. (PCS10965; p7, lines7-11)

The veterinary practitioner, or one skilled in the art, will be able to determine the dosage suitable for the particular individual patient, which may vary with the species, age, weight and response of the particular patient, as well as the bacterial species involved. The above dosages are exemplary of the average case. Accordingly, higher or lower dosage ranges may be warranted, depending upon the above factors, and are within the scope of this invention.

Compounds of Formula I may be administered either alone or in combination with one or more agents used in the treatment or prophylaxis of disease or in the reduction or suppression of symptoms. Examples of such agents (which are provided by way of illustration and should not be construed as limiting) include antiparasitics, eg arylpyrazoles such as fipronil, lufenuron, imidacloprid, avermectins (eg abamectin, ivermectin, doramectin, selamectin), milbemycins, organophosphates, pyrethroids; antihistamines, eg chlorpheniramine, trimeprazine, diphenhydramine, doxylamine; antifungals, eg fluconazole, ketoconazole, itraconazole, griseofulvin, amphotericin B; antibacterials, eg enroflaxacin, marbofloxacin, ampicillin, amoxycillin; anti-inflammatories eg prednisolone, betamethasone, dexamethasone, carprofen, ketoprofen; steroids or other antipruritic agents; dietary supplements, eg gamma-linoleic acid; and emollients. Therefore, the invention further provides for uses, etc., of compounds of formula (I) and one or more selected compounds from the above list as a combined preparation for simultaneous, separate or sequential use in the treatment of diseases or conditions according to the invention.

The composition of the formulations may optionally contain auxiliary ingredients, as known in the art, such as buffers, bulking agents, diluents, co-solvents, solvents, preservatives, chelating agents, antioxidants, tonicity adjusters, whose presence may help to provide a rapidly soluble freeze-dried product or extend the storage time of the formulation.

An example of a possible solvent and co-solvent is ethanol. An example of a chelating agent is ethylenediaminetetraacetic acid. An example of an antioxidant is ascorbic acid. An example of a tonicity adjuster is dextrose. Furthermore, the compound of Formula I may be the sole therapeutic agent in the compositions of the invention or a combination with other antibiotics or with a β-lactamase inhibitor may be employed. (U.S. Pat. No. 6,020,329; Col 16, lines 15-18)

Unlike most cephalosporins with typical broader pH ranges of stability, it was determined that formulations of Compound I with or without various buffers have a relatively narrow range of stability between a pH of about 5.0 to about 8.0. In particular, and in a preferred embodiment, optimal solution and solid state stability are achieved at a pH of about 6.0 to about 7.5. Adjustment of pH may be accomplished by either titrating to the desired pH range with, for example, a 10% solution of sodium hydroxide or hydrochloric acid, or using an appropriate buffer. Typical buffers include phosphate, acetate, citrate, carbonate, and glycine. In a preferred embodiment, phosphate is used as a buffer. In a more preferred embodiment, citrate is used as a buffer.

The water-soluble bulking agent suitable for use in the present invention can be any of the pharmaceutically acceptable inert solid materials typically used for lyophilization. Bulking agents may improve stability and/or provide a more rapidly soluble freeze-dried product. Such bulking agents include, for example, sugars such as glucose, maltose, sucrose and lactose; polyalcohols such as sorbitol and mannitol; amino acids such as glycine; polymers such as polyvinylpyrrolidone; polysaccharides such as dextran; certain inorganic salts such as sodium or potassium phosphates, or sodium chloride.

The ratio of the weight of the bulking agent to the weight of Compound I used in the compositions of the present invention should generally be within the range of from about 0.01 to about 100, depending upon the bulking agent utilized. In a preferred embodiment, polyhydroxy compounds are the bulking agent of choice. In a more preferred embodiment, sucrose is the bulking agent and was found to stabilize the sodium salt of Compound I when co-lyophilized therewith.

The optimum ratio of sucrose/Compound I, however, was unpredictable, absent experimentation. For example, it was determined that, compared to formulations without sucrose additions, a relatively small amount of sucrose (e.g. sucrose/sodium salt of Compound I ratio of 0.4) increased the extent of degradation of the sodium salt of Compound I. On the other hand, a sucrose/sodium salt of Compound I ratio of 1 exhibited similar stability as formulations wherein no sucrose was added. Ratios greater than 1.0, however, increased the stability of formulations of the sodium salt of Compound I. In a preferred embodiment, the sucrose/sodium salt of Compound I ratio ranges from greater than 1.0 to about 10. In an even more preferred embodiment, the sucrose/sodium salt of Compound I ratio is about 3.

Higher sucrose/Compound ratios may be utilized. A high sucrose concentration is limited, however, by practical considerations of viscosity of high concentrated solution, impacting syringibility of the reconstituted solution. Furthermore, high sucrose concentrations may create injection site intolerance for injectable preparations. As a general rule, viscosity of 25-30 mPa·s (millipascals·second), wherein "·" is defined as "multiplied by", can be considered as an upper limit for injectable preparations in the pharmaceutical industry. This translates to an approximate maximum 60% sucrose solution at 40° C. (M.Mathlouthi, J. Génotelle, in: M.Mathlouthi, Sucrose. Properties and Applications, Blackie Academic & Professional, London, 1995, p. 137). For example, if the concentration of Compound I in solution is 6% by weight, the acceptable sucrose/Compound I ratio would be 10:1. If Compound I concentration is 3%, the acceptable sucrose/Compound I ratio would be 20:1. These are but two examples of many possible ratios.

Antimicrobial preservatives are frequently added to pharmaceutical formulations to prevent microbial contamination. As used herein, the word "preservative" means a compound, or combination of compounds, added to prevent or inhibit the growth of micro-organisms which could present a risk of infection or degradation of the medicinal product. Generally, the level of efficacy obtained varies according to the chemical structure of the preservative, its concentration and the physical and chemical characteristics of the medicinal product (especially pH). The design of the pack and the temperature at which the product is stored will also affect the level of activity of any antimicrobial preservatives present. Useful preservatives may include m-benzoic acid and its salts, sorbic acid and its salts, alkyl esters of parahydroxybenzoic acid, phenol, chlorobutanol, benzyl alcohol, thimerosal, benzalkonium chloride, benzethonium chloride, cetylpyridinium chloride, m-cresol and chlorocresol. Mixtures of the aforementioned preservatives may also be employed.

In the present invention, formulations of Compound I containing antimicrobial preservatives were effective in satisfying United States Pharmacopeia (hereinafter "USP") criteria for antimicrobial effectiveness. In particular, various formulations of the following preservatives were found to satisfy USP criteria, for example, methyl paraben, propylparaben, m-cresol and benyzl alcohol. To satisfy European Pharmacopeia (hereinafter "EP") criteria for antimicrobial effectiveness, however, other preservatives were more appropriate (e.g. benzethonium chloride and combinations of several preservatives such as methylparaben, propylparaben and benzyl alcohol, in one combination, and methyl paraben and m-cresol in another combination.

Formulations of Compound I can be isolated by drying, preferably by lyophilization as known in the art. Usually the lyophile formulations are produced with ampule lyophilization, vial lyophilization, tray lyophilization, or like conventional methods by cooling the formulations at subzero temperature to freezing. The frozen material is then dried under vacuum by subliming the water component originally contained in the solution as a solvent, thus leaving a solid lyophilized cake. Thus, for example, the excipients described above, Compound I, or the pharmaceutically acceptable salt of Compound I, are successively dissolved under stirring in a suitable amount of water for injections. Then, further water is added to reach the desired final volume. The resulting solution is clarified, sterile filtered and aseptically distributed in sterile containers (e.g. vials) of desired capacity. Freeze-drying the solution is then performed and the vials are hermetically sealed according to conventional procedures.

The lyophilized drug product is amorphous Compound I, and more preferably the sodium salt thereof. When a product solution is required, it can be reconstituted by dissolving the dry formulation in water for injection, bacteriostatic water for injection or another pharmaceutically acceptable diluent (e.g. isotonic solution of sodium chloride, water for injection with ethanol or citrate buffer, and bacteriostatic water for injection with benzyl alcohol) in an amount sufficient to generate a solution of the required strength for parenteral administration to patients.

An amount of Compound I may be administered such that the composition provides the desired therapeutical effect as disclosed in U.S. Pat. Nos. 6,001,997, 6,020,329 and 6,077,952. The injectable reconstituted solutions of the invention may be administered, according to a variety of possible dose schedules.

EXAMPLES

To confirm the advantageous effects of the present invention, the sodium salt of Compound I, was formulated into lyophilized injectable preparations and stability of the formulations was measured.

The examples below are intended to illustrate particular embodiments of the invention and are not intended to limit the specification, including the claims, in any manner.

A. Stabilization of Lyophilized Formulations by pH Adjustment.

The formulations described in Tables 3-6, demonstrate the increased instability of compositions, both buffered and unbuffered, outside the pH range of about 5.0 to about 8.0. As set forth below in Tables 3 and 4, the sodium salt of Compound I was dissolved in either deionized water or in citrate buffer solutions at 5 mg/mL.

For formulations 1-5, solution pH was adjusted with a 10% solution of hydrochloric acid after dissolution of the sodium salt of Compound I (TABLE 3). For formulations 6-13, a buffered solution was prepared with citrate and adjusted with a 10% sodium hydroxide solution, upon which the sodium salt of Compound I was dissolved therein (TABLE 4). One mL aliquots of solutions of the sodium salt of Compound I were filled in 10 mL vials, and lyophilized using a FTS Kinetics freeze dryer (FTS Systems, Stone Ridge, N.Y.). During lyophilization, the compositions were frozen using a two-step freezing protocol (at −25° C. and −40° C.), followed by primary drying at −27° C. for approximately 22 hours, followed by a secondary drying with increased steps of temperature to 0° C., 25° C. and 50° C. The pressure during primary and secondary drying was set at 60 millitorr.

Examples of the solution preparation procedures are given below.

TABLE 3

Composition of formulations with HCl.

| Formulation # | Compound I (mg/vial) | HCl* | pH |
|---|---|---|---|
| 1 | 50 | + | 3.5 |
| 2 | 50 | + | 3.9 |
| 3 | 50 | + | 4.1 |
| 4 | 50 | + | 5.1 |
| 5 | 50 | − | 6.0 |

"+" sign means that HCl was added to the formulation whereas "−" sign indicates that HCl was not added.

TABLE 4

Composition of formulations with Citric Acid.

| Formulation # | Compound I (mg) | Citric acid (mg) | pH* |
|---|---|---|---|
| 6 | 50 | 9.6 | 5.0 |
| 7 | 50 | 9.6 | 5.5 |
| 8 | 50 | 9.6 | 5.7 |
| 9 | 50 | 9.6 | 6.0 |
| 10 | 50 | 9.6 | 6.2 |
| 11 | 50 | 9.6 | 6.5 |
| 12 | 50 | 9.6 | 6.8 |
| 13 | 50 | 9.6 | 7.0 |
| 14 | 50 | − | 6.1 |

*pH of the solutions were adjusted to the specified values with 10% sodium hydroxide solution prior to lyophilization.

The samples were stored at 40° C. for 12 weeks. The remaining amount of Compound I was then measured by reverse-phase High Pressure Liquid Chromatography ("HPLC"), using a Waters (Milford, Mass.) HPLC system with an Ultraviolet ("UV") detector set at 256 nm and a Kromasil C4 column (MetaChem Technologies Inc., Torrance, Calif.). A gradient method was utilized with mobile phase A consisting of 9:1 ratio v/v 0.025M sodium phosphate buffer solution, pH 6.5: acetonitrile, and mobile phase B consisting of 4:6 ratio v/v 0.025M sodium phosphate buffer solution, pH 6.5: acetonitrile.

Degradation results are reported at Tables 5 and 6 as percentage (%) of initial purity of Compound I. Degradation of the formulation after 18 months storage at a controlled room temperature of 25° C. (i.e. typical shelf storage conditions) was calculated using the pseudo-zero order model and the Arrhenius equation with an activation energy of 10 kcal/mol (e.g., K. A. Connors, Chemical Kinetics, 1990, VCH Publishers, Inc., New York). At this activation energy, the degradation rate constant at 40° C. ($k_{40}$) is equal to $2.27*k_{25}$ ($k_{25}$ is the degradation rate constant at 25° C.). A person of ordinary skill in the art would appreciate the reasonableness of this assumption, based on data reported by Pikal et al. for other amorphous cephalosporin compounds wherein, $k_{40}=2.2*k_{25}$. (M. J.Pikal, K. M. Dellerman, Stability testing of pharmaceuticals by high-sensitivity isothermal calorimetry at 2520 C.: cephalosporins in the solid and aqueous solution states, Int. J. Pharm. 50 (1989) 233-252).

As set forth in Table 5, formulations 4 and 5 (respectively, pH of 5.1 and 6.0, from Table I) had an acceptable long-term stability, (i.e. degradation after 18 months at 25° C. is less than 10%). Formulations with a pH less than or equal to 4.1, however, demonstrated degradation at greater than 10%, which is typically unacceptable in the pharmaceutical industry for pharmaceutical products. As demonstrated in Table 4, the optimal stability for formulations utilizing a citrate buffer, however, was between pH of about 6.0 to 7.0.

TABLE 5

Percent Compound I after 12 weeks storage at 40° C. and estimated shelf life at controlled room temperature 25° C.

| Formulation # | 12 weeks (40° C.) | % Degradation after 12 weeks (40° C.) | % Degradation* after 18 months (25° C.) |
|---|---|---|---|
| 1 | 91.3 | 8.7 | 19 |
| 2 | 94.3 | 5.7 | 15 |
| 3 | 95.9 | 4.1 | 11 |
| 4 | 96.9 | 3.1 | 8 |
| 5 | 97.2 | 2.8 | 7 |

*Calculated as described in the text

TABLE 6

Percent Compound I after 12 weeks storage at 40° C. and estimated shelf life at controlled room temperature 25° C.

| Formulation # | 12 weeks (40° C.) | % Degradation after 12 weeks (40° C.) | % Degradation* after 18 months (25° C.) |
|---|---|---|---|
| 6 | 97.5 | 2.5 | 7 |
| 7 | 98.0 | 2.0 | 5 |
| 8 | 98.6 | 1.4 | 4 |
| 9 | 98.7 | 1.3 | 3 |
| 10 | 98.9 | 1.1 | 3 |
| 11 | 99.1 | 0.9 | 2 |
| 12 | 99.2 | 0.8 | 2 |
| 13 | 99.1 | 0.9 | 2 |
| 14 | 99.2 | 0.8 | 2 |

*Calculated as described in the text

Examples of solution preparation for the above stability studies of lyophilized specific concentrations as follows:

Example 1

Formulation without pH Adjustment 1.0453 grams of the sodium salt of Compound I were dissolved in 20.0 mL de-ionized water. One mL aliquots of the resulting solution were transferred to 10-mL vials, partially stoppered with lyo-stoppers, lyophilized and hermetically capped, as described hereinabove.

Example 2

Formulation with pH Adjusted by HCl 0.5085 grams of the sodium salt of Compound I were dissolved in 10.0 mL de-ionized water. The solution was titrated with 0.1 N hydrochloric acid to pH 3.87. One mL aliquots of the resulting solution were transferred to 10-mL vials, partially stoppered with lyo-stoppers, lyophilized and hermetically capped, as described hereinabove.

Example 3

Formulation with pH Adjusted by Citrate Buffer 0.6 grams of the sodium salt of Compound I were dissolved in 12 mL of 0.05M citrate buffer at pH of 6.0. The resulting solution was filtered and 1 mL aliquots were transferred to 10-mL vials, partially stoppered with lyo-stoppers, lyophilized and hermetically capped, as described hereinabove.

B. Stabilization of lyophilized formulation of the sodium salt of Compound I by Bulking Agents.

In each experiment, formulations of the sodium salt of Compound I and sucrose, at different sucrose/sodium salt of Compound I ratios (TABLE 7), were lyophilized according to standard industry procedures, as described hereinabove. Formulations 15 to 18 and 19 to 22 were prepared independently for quality control reproducibility purposes. Stability measurements of formulations 19 to 22 were only taken at 12 weeks.

TABLE 7

Composition of formulations

| Formulation # | Compound I (mg/vial) | Sucrose (mg/vial) | Sucrose/Compound I Ratio |
|---|---|---|---|
| 15 | 50 | 0 | 0 |
| 16 | 50 | 20 | 0.4 |
| 17 | 50 | 50 | 1.0 |
| 18 | 50 | 150 | 3.0 |
| 19 | 50 | 0 | 0 |
| 20 | 50 | 20 | 0.4 |
| 21 | 50 | 50 | 1.0 |
| 22 | 50 | 150 | 3.0 |

The samples were stored at 40° C. for up to 12 weeks. The remaining amount of Compound I was measured by reverse-phase HPLC using gradient solvent method, as described above, and reported as percentage (%) of remaining Compound I. The results, as set forth in TABLE 8, demonstrate that additions of sucrose at a ratio of 3:1 (sucrose/sodium salt of Compound I) improved stability. A lower sucrose/sodium salt of Compound I ratio of 2:5 sucrose was less desirable. Stability of formulation with 1:1 ratio was similar to the formulation without sucrose.

TABLE 8

Percent Compound I after 12 weeks at 40° C.

| Formulation # | 1 week | 2 weeks | 4 weeks | 6 weeks | 12 weeks |
|---|---|---|---|---|---|
| 15 | 100.0 | 99.8 | 99.1 | 99.0 | 97.4 |
| 16 | 98.0 | 97.7 | 97.4 | 96.5 | 94.6 |
| 17 | 99.5 | 99.3 | 98.7 | 98.3 | 96.9 |
| 18 | 101 | 101 | 101 | 100 | 99.5 |
| 19 | — | — | — | — | 98.5 |
| 20 | — | — | — | — | 96.5 |
| 21 | — | — | — | — | 97.5 |
| 22 | — | — | — | — | 99.1 |

An example of solution preparation for the above stability studies of lyophilized formulations are is follows:

Example 4

Formulation with Sucrose 0.4818 grams of the sodium salt of Compound I and 0.1964 grams of sucrose were dissolved in 10 mL of de-ionized water. The resulted solution was filled in 1-mL aliquots in 10-mL vials, partially stoppered with lyo-stoppers and lyophilized, as described hereinabove. At the end of the lyophilization cycle, the vials were hermetically capped.

C. Preservatives.

Generally, preservatives are not required for cephalosporin formulations, including formulations of Compound I. Formulations stored in multi-dose containers versus single dose containers, however, require the addition of preservatives to satisfy antimicrobial effectiveness in vitro. Various formulations prepared in accordance with the working Examples hereinafter were tested for antimicrobial activity in vitro. Antimicrobial Effectiveness Tests (hereinafter "AET") were performed according to European Pharmacopoeia (EP) Procedures (European Pharmacopoeia, 3d edition, Supplement 201, Council of Europe, Strasbourg) and United States Pharmacopeia (USP) procedures (U.S. Pharmacopeia, and National Formulary USP24 NF19, 2000, United States Pharmacopeia Convention Inc., Rockville, Md.). The effectiveness of formulations containing preservatives and the sodium salt of Compound I is demonstrated in the following examples:

Example 5

AET of the Sodium Salt of Compound I and Methylparaben (1.8 mg/mL)

AET were conducted on a solution containing the sodium salt of Compound I(80 mg/mL) and methylparaben (1.8 mg/mL) in 20 mM citrate buffer. The results of AET are provided in Table 9. The formulation satisfied USP criteria (see Table 12 for acceptance criteria) for all microorganisms. Furthermore, the formulation satisfied criteria A for all microorganisms, except for S. aureus at 6 and 24 hours time points.

TABLE 9

Log reduction of microbial concentration. Formulation of the sodium salt of Compound I and Methylparaban

| Microorganism | 6 Hours | 24 Hours | 7 Days | 14 Days |
| --- | --- | --- | --- | --- |
| Aspergillus niger | — | — | 5.06* | 5.06 |
| Candida albicans | — | — | 5.17* | 5.17 |
| E. coli | — | — | 5.54* | 5.54 |
| Ps. aeruginosa | 5.16 | 5.16 | 5.16* | 5.16 |
| S. aureus | 0.10 | 0.10 | 5.12* | 5.12 |

*Corresponds to "no recovery" of microorganisms.

Example 6

AET of the Sodium Salt of Compound I, Methylparaben (1.8 mg/mL) and Propylparaben (0.2 mg/mL)

AET, according to EP and USP Procedures, were conducted on a solution containing the sodium salt of Compound I (80 mg/mL), methylparaben (1.8 mg/mL) and propylparaben (0.2 mg/mL) in 20 mM citrate buffer. The results of AET are provided in Table 8. The formulation satisfied USP criteria (see Table 14 for acceptance criteria) for all microorganisms. Furthermore, the formulation satisfied EP criteria A for all microorganisms, except for S. aureus at 6 and 24 hours time points.

TABLE 10

Log reduction of microbial concentration. Formulation of the sodium salt of Compound 1, Methylparaban and propylparaben.

| Microorganism | 6 Hours | 24 Hours | 7 Days | 14 Days |
| --- | --- | --- | --- | --- |
| Aspergillus niger | — | — | 5.06 | 5.06 |
| Candida albicans | — | — | 5.17 | 5.17 |
| E. coli | — | — | 5.54 | 5.54 |
| Ps. aeruginosa | 5.16 | 5.16 | 5.16 | 5.16 |
| S. aureus | 0.06 | 0.24 | 5.12 | 5.12 |

Example 7

AET of the Sodium Salt of Compound I and M-cresol (3 mg/ml)

AET, performed according to EP and USP Procedures, were conducted on a solution of the sodium salt of Compound I (80 mg/mL) and m-cresol (3 mg/mL) prepared by reconstitution of a lyophilized cake of the sodium salt of Compound I with Bacteriostatic Water containing 3 mg/mL m-cresol. The results of AET are provided in Table 11. The formulation satisfied USP criteria (see Table 14 for acceptance criteria) for all microorganisms. Furthermore, the formulation satisfied EP criteria A for all microorganisms, except for S. aureus at 6 hours time point.

TABLE 11

Log reduction of microbial concentration. Formulation of the sodium salt of Compound I and m-cresol.

| Microorganism | 6 Hours | 24 Hours | 7 Days |
| --- | --- | --- | --- |
| Aspergillus niger | — | — | 4.82* |
| Candida albicans | — | — | 5.24* |
| E. coli | — | — | 5.41* |
| Ps. aeruginosa | 3.35 | 4.76 | 5.36* |
| S. aureus | 1.56 | 4.76 | 5.61* |

*Corresponds to "no recovery" of microorganisms.

Example 8

AET of the Sodium Salt of Compound I, Methylparaben, Propylparaben and Benzyl Alcohol AET, performed according to EP and USP Procedures, were conducted on a solution of the sodium salt of Compound I (80 mg/mL), methylparaben (1.8 mg/mL), propylparaben (0.2 mg/mL) and benzyl alcohol (8.6 mg/mL) and 20 mM of citrate buffer, prepared by reconstitution of a lyophilized cake of the sodium salt of Compound I, methylparaben and propylparaben with bacteriostatic water for injection containing at least 9 mg/mL benyzl alcohol. Methylparaben and propylparaben were included in the lyophilized cake whereas benzyl alcohol was added with bacteriostatic water for injection. The results of AET are provided in Table 12. The formulation satisfied USP criteria (see Table 14 for acceptance criteria) for all microorganisms. Furthermore, the formulation satisfied EP criteria A for all microorganisms.

TABLE 12

Log reduction of microbial concentration. Formulation of the sodium salt of Compound I, methylparaben, propylparaben and benzyl alcohol.

| Microorganism | 6 Hours | 24 Hours | 7 Days |
| --- | --- | --- | --- |
| Aspergillus niger | — | — | 4.82 |
| Candida albicans | — | — | 5.24 |
| E. coli | — | — | 5.41 |
| Ps. aeruginosa | 5.36 | 5.36 | 5.36 |
| S. aureus | 2.71 | 5.61 | 5.61 |

Example 9

AEP of the Sodium Salt of Compound I, M-cresol and Methylparaben

AET, performed according to EP Procedure, were conducted on a solution of the sodium salt of Compound I (80 mg/mL), methylparaben (1.8 mg/mL) and m-cresol (3 mg/mL), prepared by reconstitution of a lyophilized cake of the sodium salt of Compound I with bacteriostatic water for injection containing methylparaben and m-cresol. The results of AET are provided in Table 13. The formulation satisfied EP Criteria A (see Table 14 for acceptance criteria) for *S. auereus*.

TABLE 13

Log reduction of microbial concentration.
Formulation of the sodium salt of Compound I, m-cresol and methylparaben.

| Microorganism | 6 Hours | 24 Hours |
|---|---|---|
| *S. aureus* | 4.05 | 5.20 |

TABLE 14

AET Acceptance Criteria (USP and EP)

| Microorganism | Criteria | Log Reduction | | | | |
| | | 6 Hours | 24 Hours | 7 Days | 14 Days | 28 Days |
|---|---|---|---|---|---|---|
| Bacteria | EP criteria A | 2 | 3 | — | — | NR |
| | EP criteria B | — | 1 | 3 | — | NI |
| | USP cat 1A | — | — | 1.0 | 3.0 | NI |
| Fungi | EP criteria A | — | — | 2 | — | NI |
| | EP criteria B | — | — | — | 1 | NI |
| | USP cat 1A | — | — | NI | NI | NI |

NR = no recovery; NI = no increase

European Pharmacopoeia, 3d edition, Supplement 2001, Council of Europe, Strasbourg; U.S. Pharmacopeia, and National Formulary USP24 NF19, 2000, United State Pharmacopeial Convention Inc., Rockville, Md.

The invention claimed is:

1. A lyophilized pharmaceutical composition comprising a compound of Formula I,

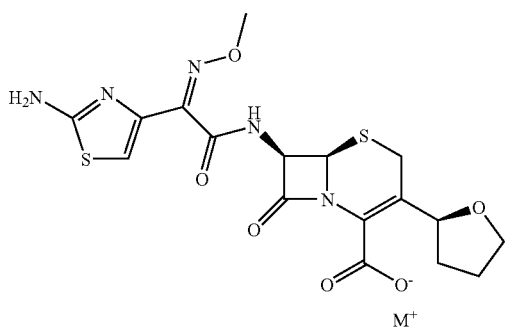

wherein M+ is Na+, an optional pharmaceutically acceptable buffer, and a pharmaceutically acceptable preservative selected from methyl paraben, propyl paraben, or a combination of methyl and propyl parabens, wherein the aqueous composition, prior to lyophilization, has a pH of 6.0 to 7.5, and wherein the composition after lyophilization has a residual water content of less than 1% by weight, based on the weight of the lyophile.

2. A composition according to claim 1, wherein the buffer is a citrate buffer.

3. A kit comprising:
a) a therapeutically effective amount of a lyophilized pharmaceutical composition comprising a compound of Formula I,

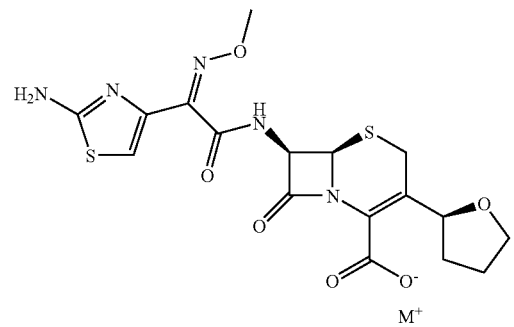

wherein M+ is N+, an optional pharmaceutical buffer, and a preservative selected from methyl paraben, propyl paraben, or a combination of methyl and propyl parabens, wherein the aqueous composition, prior to lyophilization, has a pH of 6.0 to 7.5, and wherein the composition after lyophilization has a residual water content of less than 1 by weight, based on the weight of the lyophile;

b) an aqueous pharmaceutically acceptable diluent; and c) a first and second container for containing the composition (a) and the diluent (b), wherein the first container is adapted to receive the diluent from the second container.

4. A composition according to claim 1 wherein the composition after lyophilization has a residual water content of less than 0.5% by weight, based on the weight of the lyophile.

5. A composition according to claim 4, wherein the buffer is a citrate buffer.

6. A kit comprising:
a) a therapeutically effective amount of a lyophilized pharmaceutical composition comprising a compound of Formula I;

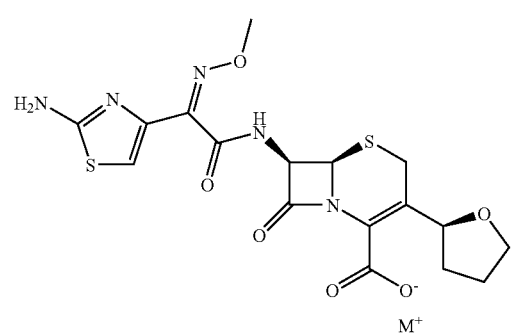

wherein M+ is Na+, an optional pharmaceutical buffer, and a preservative selected from methyl paraben, propyl paraben, or a combination of methyl and propyl parabens, wherein the aqueous composition, prior to lyophilization, has a pH of 6.0 to 7.5, and wherein the composition after lyophilization has a residual water content of less than 0.5% by weight, based on the weight of the lyophile;

b) an aqueous pharmaceutically acceptable diluent; and c) a first and second container means for containing the composition (a) and the diluent (b), wherein the first container is adapted to receive the diluent from the second container.

* * * * *

UNITED STATES PATENT AND TRADEMARK OFFICE
CERTIFICATE OF CORRECTION

PATENT NO. : 7,378,408 B2
APPLICATION NO. : 10/292343
DATED : May 27, 2008
INVENTOR(S) : Kimball et al.

It is certified that error appears in the above-identified patent and that said Letters Patent is hereby corrected as shown below:

Column 20, line 23: "wherein M+ is N+," should read "wherein M+ is Na+,"

Signed and Sealed this

Eighteenth Day of November, 2008

JON W. DUDAS
*Director of the United States Patent and Trademark Office*